US009772551B2

(12) United States Patent
Terasawa et al.

(10) Patent No.: US 9,772,551 B2
(45) Date of Patent: Sep. 26, 2017

(54) EVALUATION METHOD OF DEFECT SIZE OF PHOTOMASK BLANK, SELECTION METHOD, AND MANUFACTURING METHOD

(71) Applicant: SHIN-ETSU CHEMICAL CO., LTD., Tokyo (JP)

(72) Inventors: Tsuneo Terasawa, Joetsu (JP); Takahiro Kishita, Joetsu (JP); Daisuke Iwai, Joetsu (JP); Hiroshi Fukuda, Joetsu (JP); Atsushi Yokohata, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 199 days.

(21) Appl. No.: 14/921,076

(22) Filed: Oct. 23, 2015

(65) Prior Publication Data

US 2016/0116837 A1     Apr. 28, 2016

(30) Foreign Application Priority Data

Oct. 24, 2014  (JP) ................. 2014-217386

(51) Int. Cl.
| | | |
|---|---|---|
| *G03F 1/84* | (2012.01) | |
| *G03F 1/50* | (2012.01) | |
| *G01N 21/88* | (2006.01) | |
| *G01N 21/956* | (2006.01) | |
| *G01N 21/95* | (2006.01) | |

(52) U.S. Cl.
CPC ........... *G03F 1/84* (2013.01); *G01N 21/8851* (2013.01); *G01N 21/956* (2013.01); *G03F 1/50* (2013.01); *G01N 2021/8874* (2013.01); *G01N 2021/9511* (2013.01); *G01N 2021/95676* (2013.01)

(58) Field of Classification Search
CPC ......... G03F 1/50; G03F 1/84; G01N 21/8851; G01N 21/956; G01N 2021/8874; G01N 2021/9511; G01N 2021/95676
USPC .................................. 430/5, 22, 30; 382/144
See application file for complete search history.

(56) References Cited

U.S. PATENT DOCUMENTS

| 6,617,603 B2 | 9/2003 | Ishiguro et al. |
| 7,379,176 B2 | 5/2008 | Sekine et al. |
| 7,551,273 B2 | 6/2009 | Sekine et al. |

FOREIGN PATENT DOCUMENTS

| JP | 2001-174415 A | 6/2001 |
| JP | 2002-333313 A | 11/2002 |
| JP | 2005-265736 A | 9/2005 |
| JP | 2013-19766 A | 1/2013 |

*Primary Examiner* — Christopher Young
(74) *Attorney, Agent, or Firm* — Birch, Stewart, Kolasch & Birch, LLP

(57) ABSTRACT

The defect size of a photomask blank is evaluated. An inspection-target photomask blank is irradiated with inspection light and reflected light of the region of the inspection-target photomask blank irradiated with the inspection light is collected through an objective lens of an inspection optical system as a magnified image of the region. Then, an intensity change part in the light intensity distribution profile of the magnified image is identified. Next, a difference in the light intensity of the intensity change part is obtained and the width of the intensity change part is obtained as the apparent width of the defect. Then, the width of the defect is calculated on the basis of a predetermined conversion expression showing the relationship among the difference in the light intensity, the apparent width of the defect, and the actual width of the defect, and the width of the defect is estimated.

18 Claims, 10 Drawing Sheets

EVALUATION METHOD OF DEFECT SIZE OF PHOTOMASK BLANK, SELECTION METHOD, AND MANUFACTURING METHOD

CROSS-REFERENCE TO RELATED APPLICATION

This non-provisional application claims priority under 35 U.S.C. §119(a) on Patent Application No. 2014-217386 filed in Japan on Oct. 24, 2014, the entire contents of which are hereby incorporated by reference.

TECHNICAL FIELD

The present invention relates to an evaluation method of the defect size of a photomask blank used for manufacturing a photomask (mask for transfer) used in manufacturing of a semiconductor device (semiconductor equipment), and particularly to a technique effective for size evaluation of a micro-defect. Furthermore, the present invention relates to a selection method and a manufacturing method of a photomask blank to which the evaluation method of the defect size of a photomask blank is applied.

BACKGROUND ART

The semiconductor device (semiconductor equipment) is formed by repeatedly using a photolithography technique in which a photomask in which a circuit pattern is drawn is irradiated with exposure light and the circuit pattern formed in the photomask is transferred onto a semiconductor substrate (semiconductor wafer) through a reduction optical system. The photomask is manufactured by forming a circuit pattern on a substrate on which an optical film is formed (photomask blank). Such an optical film is generally a thin film composed mainly of a transition metal compound or a thin film composed mainly of a silicon compound containing a transition metal, and a film functioning as a light-blocking film or a film functioning as a phase shift film is selected according to the purpose.

The photomask is used as an original drawing for manufacturing a semiconductor element having a micro-pattern and is required to have no defect, which naturally requires the photomask blank to also have no defect. Due to such circumstances, many studies have been made on techniques for defect detection of photomask and photomask blank.

In JP-A 2001-174415 (Patent Document 1) and JP-A 2002-333313 (Patent Document 2), a method in which a substrate is irradiated with laser light and a defect and a foreign matter are detected from scattered reflection of light is described, and particularly a technique in which a detection signal is given asymmetry to discriminate whether a defect is a projected defect (bump defect) or a recessed defect (pit defect) is described. Furthermore, in JP-A 2005-265736 (Patent Document 3), a technique in which deep ultraviolet (DUV) light used for carrying out a pattern inspection of a general optical mask is used as inspection light is described. Moreover, in JP-A 2013-19766 (Patent Document 4), a technique in which inspection light is split into plural illumination spots and is scanned and each reflected beam is received by a light detecting element is described.

CITATION LIST

Patent Document 1: JP-A 2001-174415
Patent Document 2: JP-A 2002-333313
Patent Document 3: JP-A 2005-265736
Patent Document 4: JP-A 2013-19766

DISCLOSURE OF THE INVENTION

Along with continuous microminiaturization of the semiconductor device, development of techniques to improve the resolution of the photolithography technique is also being actively promoted. So far, an ArF lithography technique with use of argon fluoride (ArF) excimer laser light with a wavelength of 193 nm has been developed and applied to mass production of semiconductor devices. Furthermore, development of a lithography technique with use of extreme ultraviolet (EUV) light with a shortened wavelength, specifically a wavelength of 13.5 nm, (extreme ultraviolet lithography (EUVL)) has also been promoted. However, due to the circumstances in which it is difficult to treat this technique, the ArF lithography technique is continuously used and studies are strenuously being made on a technique in which a pattern having a size sufficiently smaller than the exposure wavelength is finally formed by employing a process called multi-patterning in which exposure process and processing process are combined plural times. In the case of this process, the minimum pattern pitch of the pattern formed by one time of exposure with one photomask is about 400 to 600 nm on a photomask that makes the length one-fourth by reduction projection (4× mask). However, because this process is premised on the multi-patterning, the fidelity of the shape of the transfer pattern and the accuracy of the pattern edge position need to be improved and a large number of micro auxiliary patterns (sub-resolution assist features) that are not transferred alone need to be formed on the photomask. Furthermore, the size of this auxiliary pattern reaches less than 100 nm on the photomask. Therefore, also in the photomask blank, defects that are fatal to generation of the micro auxiliary patterns need to be all detected, and the size of the defects reaches a 50-nm-level.

Inspection apparatuses described in the above Patent Documents 1 to 4 are all apparatuses employing an optical defect detection method. The optical defect detection method has advantages that a wide-area defect inspection in a comparatively-short time is enabled and precise detection of micro defects is also enabled through wavelength shortening of the light source. However, if the defect size is as extremely small as up to 100 nm, the influence of the defect on reflected light for the inspection is subtle. Thus, even though the existence of a defect can be detected, it is not easy to evaluate its size. In particular, the pinhole, which is a typical defect caused in deposition of the optical film of the photomask blank, is a defect about which identification of the defect size is extremely difficult.

The present invention is made in order to solve the above-described problems and an object thereof is to provide a method for obtaining the defect size with high accuracy by using an optical evaluation method of the defect size, particularly a practical method by which the defect size in a size region smaller than the nominal resolution of an inspection optical system can be evaluated easily and favorably, and a selection method and a manufacturing method of a photomask blank to which the evaluation method of the defect size of a photomask blank is applied.

The present inventors strenuously made a series of studies in order to solve the above-described problems. In the series of studies, reflected light of inspection light with which an inspection-target photomask blank was irradiated was collected through an objective lens of an inspection optical system as a magnified image of the irradiated region, and an intensity change part in the light intensity distribution profile of this magnified image was identified as a defect in the surface of the photomask blank. Furthermore, a difference ΔS in the light intensity of the intensity change part and width Wsig of the intensity change part were obtained and they were contrasted with the actual width of the defect. As a result, a correlation was found in them and the present inventors found that, by using a predetermined conversion expression representing this correlation, the actual width can be accurately estimated and evaluated in a defect whose width is smaller than the nominal resolution of the inspection optical system from the difference ΔS in the light intensity measured about the defect of the inspection target and the width Wsig of the intensity change part.

Furthermore, reflected light of inspection light with which a reference photomask blank having a defect whose width was known and was at least the nominal resolution of the inspection optical system was collected through the objective lens of the inspection optical system as a magnified image of the irradiated region, and a difference Ssat in the light intensity of an intensity change part of this magnified image was obtained. Then, with use of this difference Ssat as a constant, the above-described difference ΔS in the light intensity of the intensity change part and the width Wsig of the intensity change part were contrasted with the actual width of the defect and a correlation among them was obtained. As a result, the present inventors found that Wcal calculated on the basis of a conversion expression that is the following expression (1) favorably corresponds to the actual width of the defect even when the defect size is smaller than the nominal resolution of the inspection optical system, and reached the making of the present invention.

$$W\text{cal}=W\text{sig}\times(\Delta S/S\text{sat})^T \quad (1)$$

In the expression, T is a constant satisfying a relationship of $0.5 \leq T \leq 0.6$.

Therefore, the present invention provides the following evaluation method of the defect size of a photomask blank, the following selection method of a photomask blank, and the following manufacturing method of a photomask blank.

Accordingly, in one aspect, the present invention provides an evaluation method of defect size of a photomask blank, the evaluation method being a method for evaluating size of a defect in a surface of the photomask blank in which at least one layer of a thin film is formed over a substrate. The evaluation method includes the steps of:

(A1) preparing a reference photomask blank having a defect whose width is known and is at least nominal resolution of an inspection optical system;

(A2) aligning a position of the defect with an inspection position of the inspection optical system;

(A3) setting an optical condition of the inspection optical system;

(A4) irradiating the reference photomask blank with inspection light;

(A5) collecting reflected light of a region of the reference photomask blank irradiated with the inspection light through an objective lens of the inspection optical system as a magnified image of the region;

(A6) identifying an intensity change part in a light intensity distribution profile of the magnified image;

(A7) obtaining difference Ssat between a maximum value and a minimum value of light intensity of the intensity change part;

(B1) preparing an inspection-target photomask blank having a pinhole defect whose width is smaller than the nominal resolution of the inspection optical system;

(B2) aligning a position of the pinhole defect with the inspection position of the inspection optical system;

(B3) setting the optical condition of the inspection optical system to the optical condition set in the (A3) step;

(B4) irradiating the inspection-target photomask blank with inspection light;

(B5) collecting reflected light of a region of the inspection-target photomask blank irradiated with the inspection light through the objective lens of the inspection optical system as a magnified image of the region;

(B6) identifying an intensity change part in a light intensity distribution profile of the magnified image;

(B7) obtaining difference ΔS between a maximum value and a minimum value of light intensity of the intensity change part;

(B8) identifying both ends of the intensity change part as edges of the pinhole defect and obtaining width of the intensity change part as apparent width Wsig of the pinhole defect; and (B9) calculating Wcal from the apparent width Wsig of the pinhole defect and the differences Ssat and ΔS in the light intensity on the basis of the following expression (1) and estimating Wcal as width of the pinhole defect, $$W\text{cal}=W\text{sig}\times(\Delta S/S\text{sat})^T \quad (1)$$

wherein T is a constant satisfying a relationship of $0.5 \leq T \leq 0.6$.

In another aspect, the prevent invention further provides an evaluation method of defect size of a photomask blank, the evaluation method being a method for evaluating size of a defect in a surface of the photomask blank in which at least one layer of a thin film is formed over a substrate. The evaluation method includes the steps of:

(A1) preparing a reference photomask blank having a defect whose width is known and is at least nominal resolution of an inspection optical system;

(A2) aligning a position of the defect with an inspection position of the inspection optical system;

(A3) setting an optical condition of the inspection optical system;

(A4) irradiating the reference photomask blank with inspection light;

(A5) collecting reflected light of a region of the reference photomask blank irradiated with the inspection light through an objective lens of the inspection optical system as a magnified image of the region;

(A6) identifying an intensity change part in a light intensity distribution profile of the magnified image;

(A7a) obtaining difference Ssat between a maximum value of light intensity of the intensity change part and the light intensity at a central part of the intensity change part in width direction;

(B1) preparing an inspection-target photomask blank having a pinhole defect whose width is smaller than the nominal resolution of the inspection optical system;

(B2) aligning a position of the pinhole defect with the inspection position of the inspection optical system;

(B3) setting the optical condition of the inspection optical system to the optical condition set in the (A3) step;

(B4) irradiating the inspection-target photomask blank with inspection light;

(B5) collecting reflected light of a region of the inspection-target photomask blank irradiated with the inspection light through the objective lens of the inspection optical system as a magnified image of the region;

(B6) identifying an intensity change part in a light intensity distribution profile of the magnified image;

(B7a) obtaining difference ΔS between a maximum value of light intensity of the intensity change part and the light intensity at a central part of the intensity change part in width direction;

(B8a) obtaining width between positions of ½ of the difference ΔS of the light intensity distribution profile of the intensity change part as apparent width Wsig of the pinhole defect; and (B9) calculating Wcal from the apparent width Wsig of the pinhole defect and the differences Ssat and ΔS in the light intensity on the basis of the following expression (1) and estimating Wcal as width of the pinhole defect, $$W\text{cal}=W\text{sig}\times(\Delta S/S\text{sat})^T \quad (1)$$

wherein T is a constant satisfying a relationship of 0.5≤T≤0.6).

In the evaluation method as above, preferably a photomask blank in which a programmed defect having a predetermined width is formed is used as the reference photomask blank.

In the evaluation method as above, preferably the (A1) to (A7) steps or the (A1) to (A7a) steps are carried out on the basis of optical simulation to obtain the difference Ssat in the light intensity.

In the evaluation method as above, preferably the inspection light is light with a wavelength of 210 to 550 nm.

In the evaluation method as above, preferably in the (A4) step or the (B4) step, the photomask blank is irradiated with the inspection light while being placed on a stage that allows the photomask blank to move in in-plane direction of the photomask blank.

In the evaluation method as above, preferably in the (A4) step or the (B4) step, the photomask blank is irradiated with the inspection light by oblique illumination in which an optical axis of the inspection light is inclined to an inspected surface of the photomask blank.

In the evaluation method as above, preferably in the (A5) step or the (B5) step, the inspection optical system includes a spatial filter that partly blocks light passing through substantially a pupil position of the objective lens and collects the reflected light through the spatial filter.

In another aspect, the present invention further provides a selection method of a photomask blank, including the step of:

selecting a photomask blank that does not include a defect with size surpassing a predetermined size criterion on the basis of information on defect size obtained by the evaluation method as above.

In another aspect, the present invention further provides a manufacturing method of a photomask blank, including the steps of:

forming at least one layer of a thin film over a substrate; and evaluating size of a defect in a surface of a photomask blank in which the at least one layer of the thin film is formed over the substrate by the evaluation method as above.

Advantageous Effects of the Invention

According to the present invention, the defect size of a photomask blank can be evaluated with high accuracy by using the optical evaluation method of the defect size even in a size region smaller than the nominal resolution of the inspection optical system.

DESCRIPTION OF THE PREFERRED EMBODIMENTS

First, a step of manufacturing a photomask from a photomask blank will be described. FIGS. 1A to 1F are an explanatory diagram of one example of the step of manufacturing the photomask from the photomask blank and is sectional views of the photomask blank, an intermediate body, or the photomask at the respective stages of the manufacturing step. In the photomask blank, at least one layer of a thin film is formed over a transparent substrate.

Figure 1A:
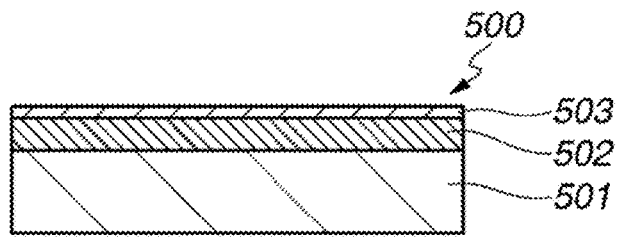
FIGS. 1A to 1F illustrate one example of a step of manufacturing a photomask from a photomask blank and are sectional views at the respective stages of the manufacturing step.
Figure 1B:
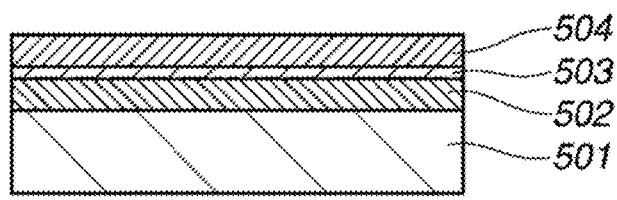
Figure 1C:
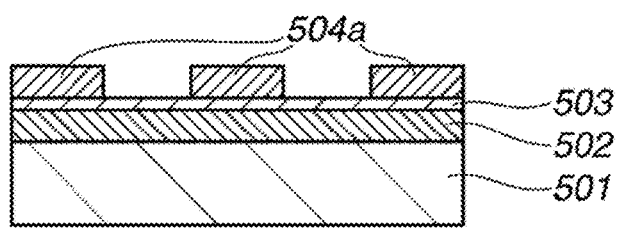
Figure 1D:
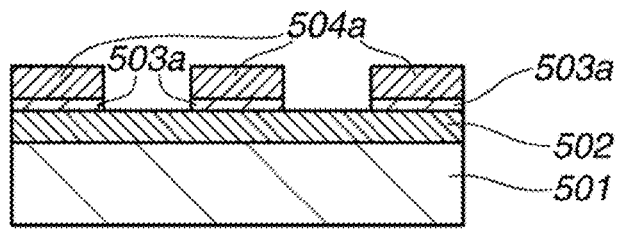
Figure 1E:
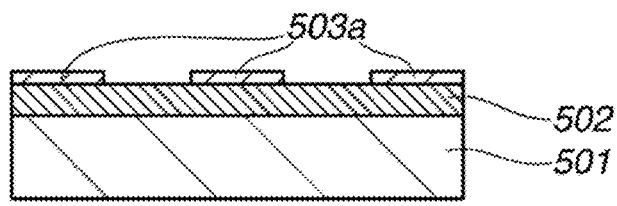
Figure 1F:
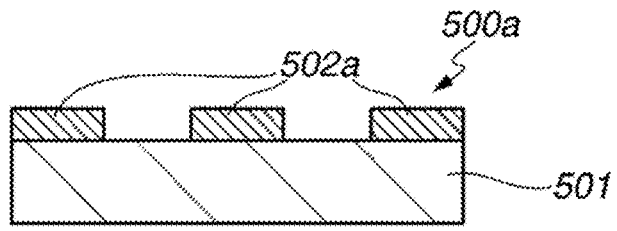

In a photomask blank 500 shown in FIG. 1A, an optical thin film 502 functioning as a light-blocking film or a phase shift film such as a halftone phase shift film is formed on a transparent substrate 501 and a hard mask film (processing assist thin film) 503 for the optical thin film 502 is formed on the optical thin film 502. In the case of manufacturing a photomask from such a photomask blank, first a resist film 504 for processing of the hard mask film 503 is formed on the hard mask film 503 (FIG. 1B). Next, through a lithography step by an electron beam drawing method or the like, a resist pattern 504a is formed from the resist film 504 (FIG. 1C). Then, by using the resist pattern 504a as an etching mask, the hard mask film 503 under the resist pattern 504a is processed to form a hard mask film pattern 503a (FIG. 1D). Then, the resist pattern 504a is removed (FIG. 1E). Moreover, by using the hard mask film pattern 503a as an etching mask, the optical thin film 502 under the hard mask film pattern 503a is processed. Thereby, an optical thin film pattern 502a is formed. Then, when the hard mask film pattern 503a is removed, a photomask 500a is obtained (FIG. 1F).

Figure 2A:
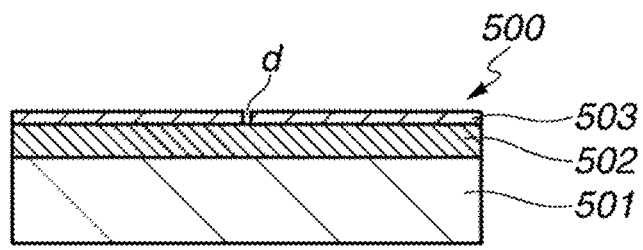
FIGS. 2A and 2B are sectional views showing examples of a photomask blank in which a defect exists and FIG. 2C is a diagram showing a photomask manufactured from the photomask blank in which the defect exists.
Figure 2B:
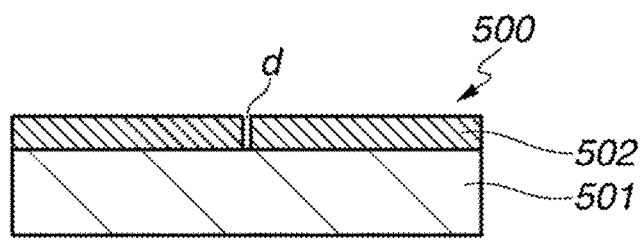
Figure 2C:
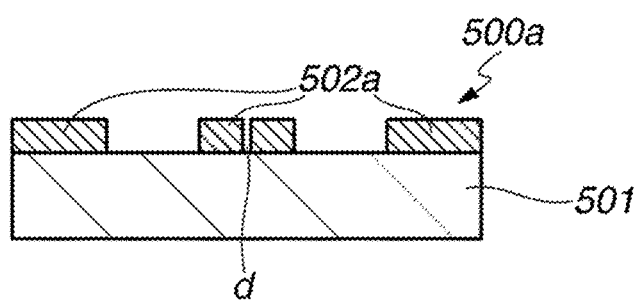

If a defect such as a pinhole exists in the thin film of the photomask blank, this defect causes a defect in a mask pattern on the photomask finally. An example of a typical defect in the photomask blank is shown in FIGS. 2A to 2C. FIG. 2A is a diagram showing an example of the photomask blank 500 in which a pinhole defect d exists in the hard mask film 503 formed on the optical thin film 502 in order to perform high-accuracy processing of the optical thin film 502. FIG. 2B is a diagram showing an example of the photomask blank 500 in which the pinhole defect d exists in the optical thin film 502 itself.

In either photomask blank, in the case of manufacturing a photomask from such a photomask blank by the manufacturing step shown in FIGS. 1A to 1F, a photomask in which the defect d derived from the photomask blank exists in the optical thin film pattern 502a like the photomask 500a shown in FIG. 2C is formed. Furthermore, this defect d becomes a factor in causing a pattern transfer error in exposure with use of the photomask. Therefore, the defect in the photomask blank needs to be detected at the stage of the photomask blank before the processing of the photomask blank, and the photomask blank having the defect needs to be excluded or the defect needs to be corrected. For such a reason, it is desired to provide a method by which a defect such as a pinhole existing in the thin film of the photomask blank, particularly a defect having a finer size that has become necessary along with microminiaturization of the semiconductor device, specifically e.g. a width of up to 100 nm, can be effectively detected by an optical technique and the size of the defect can be evaluated more easily by the optical technique.

Figure 3:
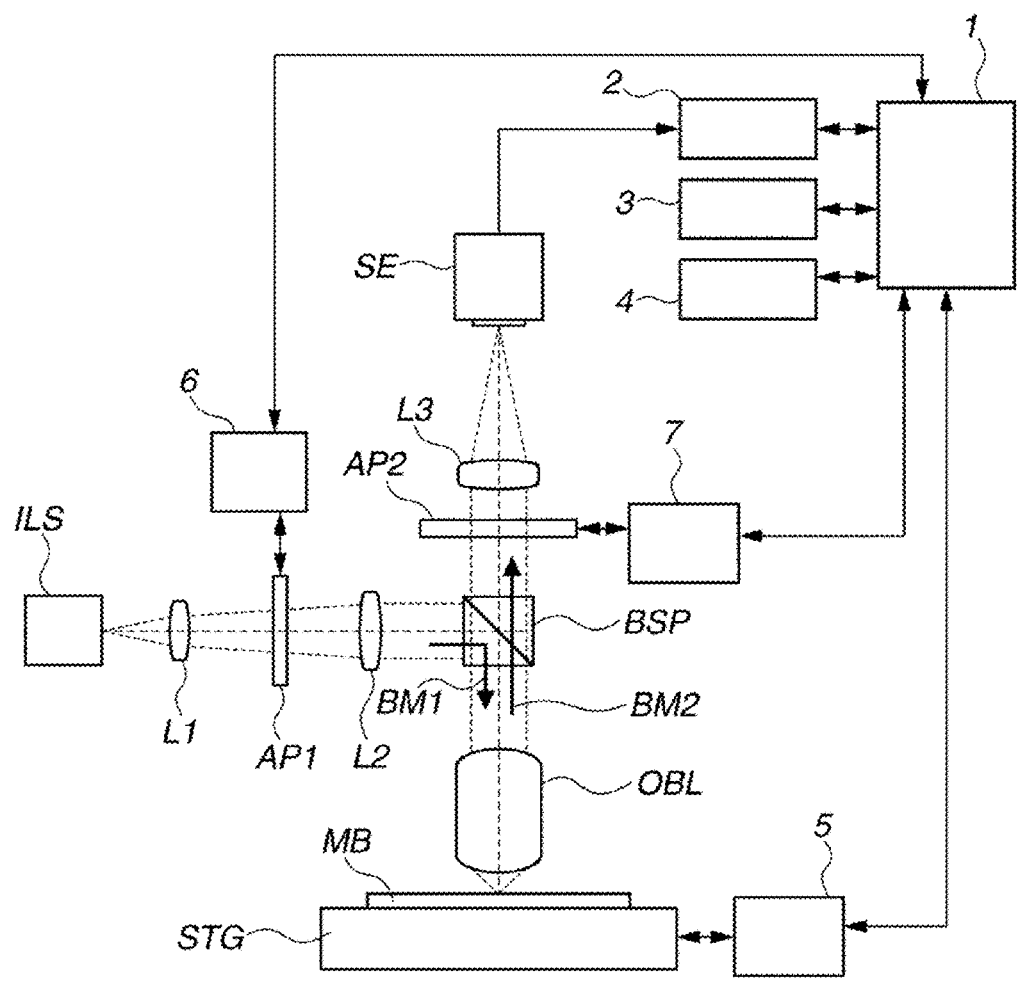
FIG. 3 is a diagram showing one example of the configuration of a defect inspection apparatus of the photomask blank.

FIG. 3 is a diagram showing one example of the basic configuration of a defect inspection apparatus of the photomask blank. As shown in FIG. 3, an inspection optical system includes a light source ILS, a beam splitter BSP, an objective lens OBL, a photomask blank MB in which an optical film is formed, and an image detector SE. In the present invention, it is preferable to use light with a wavelength of about 210 to 550 nm, specifically e.g. DUV light (light with a wavelength of about 210 to 300 nm) as inspection light. The light source ILS is configured to be capable of emitting such light and inspection light BM1 emitted from this light source ILS is made incident on the beam splitter BSP via an illumination region control aperture AP1 and a group of lenses L1 and L2. Then, the inspection light BM1 is reflected to be bent by the beam splitter BSP and a predetermined region of the photomask blank MB is irradiated with the inspection light BM1 through the objective lens OBL.

The inspection light BM1 with which the photomask blank MB is irradiated is reflected and reflected light BM2 is collected by the objective lens OBL. In addition, the reflected light BM2 is transmitted through the beam splitter BSP, an aperture stop AP2, and a lens L3 to reach the light receiving surface of the image detector SE. The position of the image detector SE is adjusted so that, at this time, a magnified inspection image of the surface of the photomask blank MB is formed on the light receiving surface of the image detector SE. By analyzing the magnified inspection image received by the image detector SE, a defect existing on the photomask blank MB can be detected. Data collected by the image detector SE is stored in an inspection image data storage 2 to be subjected to arithmetic processing to be described later. Then, defect information resulting from the arithmetic operation is stored in a memory 3.

The photomask blank MB is placed on a mask stage STG and is positioned at a position at which a defect to be evaluated can be inspected by the objective lens OBL through movement and positioning of the mask stage STG. Overall control of this positioning, the collection of inspection images, and various kinds of arithmetic processing is carried out by a system control unit 1 including a central processing unit (CPU). The system control unit 1 can carry out position control of the mask stage STG through a stage driving unit 5 and simultaneously control the illumination region control aperture AP1 through an illumination aperture driving unit 6 to implement various illumination conditions. Furthermore, the system control unit 1 can control the aperture stop AP2 through an aperture stop driving unit 7 to select various pupil filters. Moreover, this defect inspection apparatus includes a monitor 4 and displays an observation image of a defect.

The flow of an inspection method aiming at evaluation of the size of a pinhole defect in a photomask blank will be described along a flowchart shown in FIG. 4. First, a description will be made about a method for evaluating the size of a pinhole defect existing in a thin film with a comparatively-small film thickness (e.g. thickness of 2 to 30 nm, particularly 2 to 10 nm) like the hard mask film over the substrate of the photomask blank shown in FIG. 2A, i.e. a comparatively-shallow pinhole defect (e.g. with depth of 1 to 30 nm, particularly 1 to 10 nm) (first embodiment).

Figure 4:
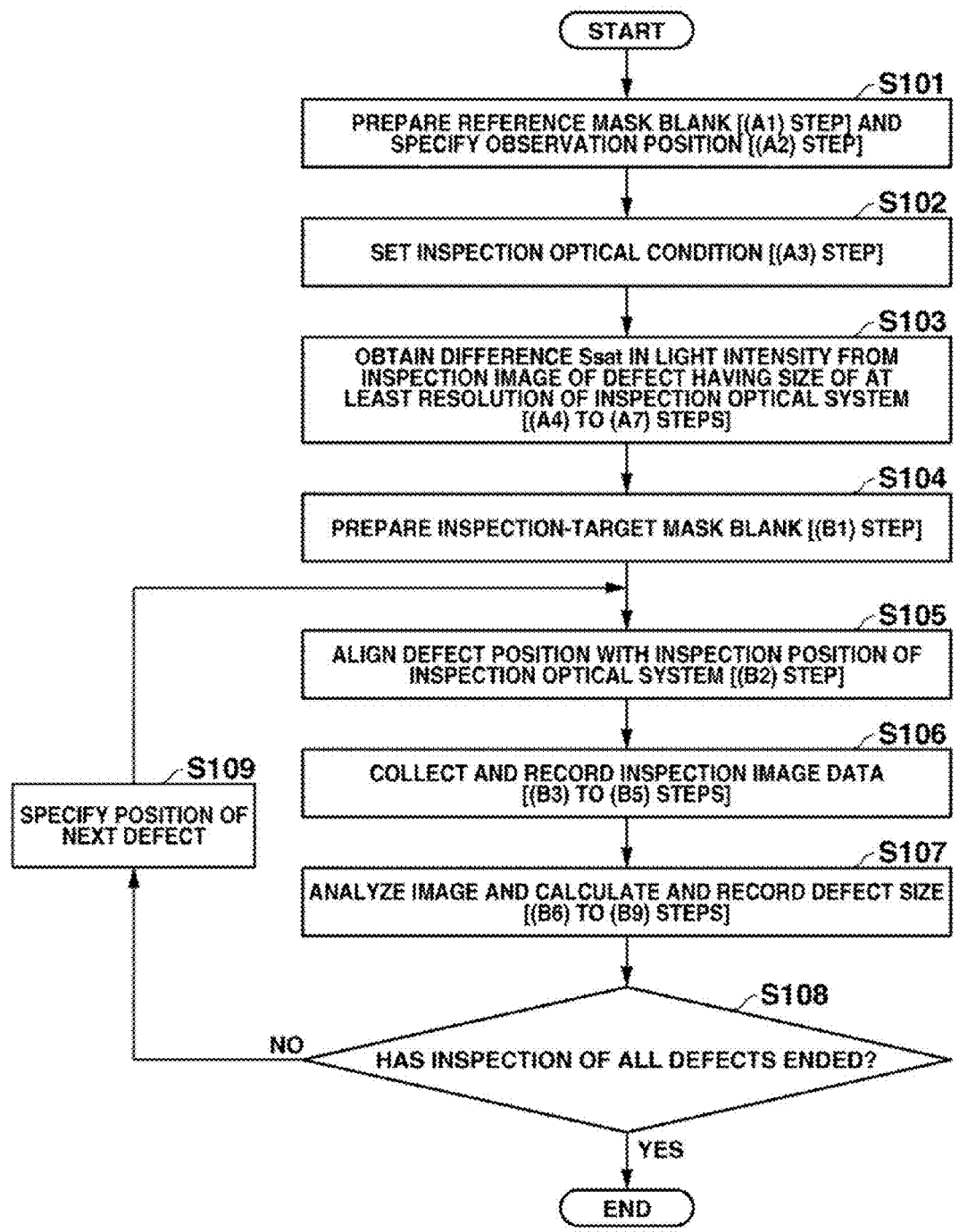
FIG. 4 is a flowchart of an evaluation method of the defect size of the photomask blank.

First, as shown in FIG. 4, as a step S101, a reference photomask blank having a defect whose width is known and is at least the nominal resolution of the inspection optical system, preferably is sufficiently larger than the nominal resolution of the inspection optical system, specifically is two to five times the nominal resolution of the inspection optical system, e.g. a photomask blank in which a programmed defect (designed defect) having a predetermined width is formed, is prepared ((A1) step), and the position of the defect is aligned with the inspection position of the inspection optical system ((A2) step). For the position alignment, specifically, the defect position coordinates of the reference photomask blank may be specified and be stored in the defect inspection apparatus. As the defect position coordinates, the position coordinates of the defect identified by a publicly-known defect inspection can be used. Next, as a step S102, an inspection optical condition is set ((A3) step). It is preferable to use e.g. light with a wavelength of 210 to 550 nm, such as DUV light (light with a wavelength of about 210 to 300 nm), as inspection light. Here, the nominal resolution of the inspection optical system is a value calculated on the basis of the Rayleigh expression defined as follows.

$$\text{resolution} = k_1 \times \lambda / NA$$

In the expression, $k_1$ is a constant specific to the inspection optical system, $\lambda$ is the wavelength of the inspection light, and NA is the numerical aperture of a lens.

Next, as a step S103, pieces of observation image data of the defect are collected and Ssat that is the difference in the light intensity of the defect part is obtained. In this step S103, the following (A4) to (A7) steps are included.

(A4) a step of irradiating the reference photomask blank with the inspection light, (A5) a step of collecting reflected light of the region of the reference photomask blank irradiated with the inspection light through the objective lens of the inspection optical system as a magnified image of the region, (A6) a step of identifying an intensity change part in the light intensity distribution profile of the magnified image, and (A7) a step of obtaining the difference Ssat between the maximum value and the minimum value of the light intensity of the intensity change part.

Furthermore, the step S103 may include the following (A8) step.

(A8) a step of identifying both ends of the intensity change part as the edges of the defect and obtaining the width of the intensity change part as apparent width Wsig of the defect.

The difference Ssat in the light intensity may be obtained by actually using a photomask blank having a defect and carrying out the (A1) step to the (A7) step or may be obtained through estimation by carrying out the (A1) to (A7) steps on the basis of optical simulation. Furthermore, with a stable inspection optical system, the difference Ssat in the light intensity does not need to be obtained for each of the respective photomask blanks of inspection targets and it is also possible to apply the obtained difference Ssat in the light intensity to evaluation of the defect size of plural inspection-target photomask blanks.

Next, as a step S104, an inspection-target photomask blank having a pinhole defect whose width is smaller than the nominal resolution of the inspection optical system is prepared ((B1) step). Next, as a step S105, the position of the pinhole defect is aligned with the inspection position of the inspection optical system ((B2) step). For the position alignment, specifically, the defect position coordinates of the inspection-target photomask blank may be stored in the defect inspection apparatus and the inspection-target photomask blank may be placed on the stage to move the stage. As the defect position coordinates, the position coordinates of the defect identified by a publicly-known defect inspection can be used.

Next, as a step S106, pieces of image data of the defect are collected and recorded. In this step S106, the following (B3) to (B5) steps are included.

(B3) a step of setting the optical condition of the inspection optical system to the optical condition set in the (A3) step, (B4) a step of irradiating the inspection-target photomask blank with the inspection light, and (B5) a step of collecting reflected light of the region of the inspection-target photomask blank irradiated with the inspection light through the objective lens of the inspection optical system as a magnified image of the region.

Next, as a step S107, image data is analyzed from the collected pieces of image data and width Wcal of the defect is calculated by using a predetermined conversion expression and is recorded.

Figure 5:
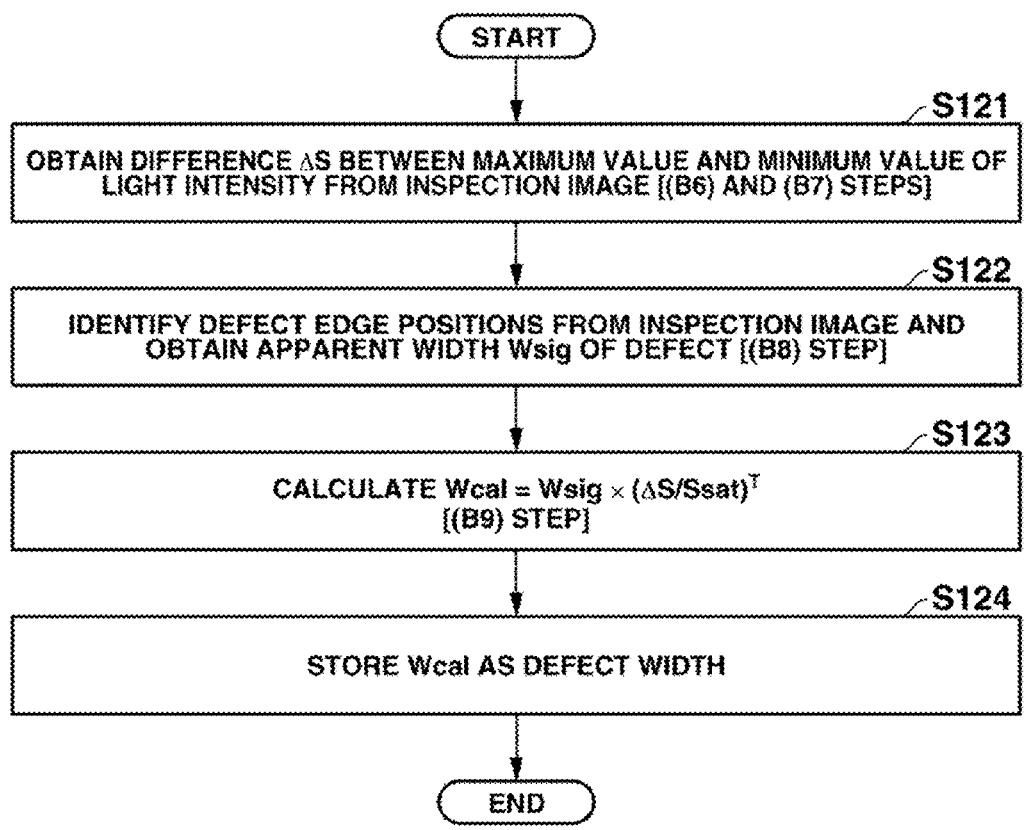
FIG. 5 is a flowchart showing one example (first embodiment) of processing of obtaining width Wcal of a defect in the evaluation method of the defect size of the photomask blank.

Here, the details of the flow of the processing of obtaining the width Wcal of the defect in the step S107 will be described along a flowchart shown in FIG. 5. First, as a step S121, an intensity change part in the light intensity distribution profile of the magnified image is identified ((B6) step) and difference ΔS between the maximum value and the minimum value of the light intensity of the intensity change part is obtained ((B7) step). Furthermore, as a step S122, both ends of the intensity change part are identified as the edges of the defect to be deemed as apparent defect edges and the width of the intensity change part is obtained as apparent width Wsig of the pinhole defect ((B8) step).

Next, as a step S123, Wcal is calculated by using Ssat, ΔS, and Wsig obtained in the (A7) step, the (B7) step, and the (B8) step on the basis of the following expression (1), and Wcal is estimated as the width of the defect ((B9) step).

$$Wcal = Wsig \times (\Delta S/Ssat)^T \qquad (1)$$

In the expression, T is a constant satisfying a relationship of 0.5≤T≤0.6.

Then, according to need, as a step S124, obtained Wcal is recorded as the width of the pinhole defect.

The value of T in the above expression (1) is a value that changes depending on the film structure or the depth of the pinhole defect (thickness of the thin film). The value of T can be calculated as follows. Specifically, with use of a standard photomask blank having a pinhole defect whose width is known and is smaller than the nominal resolution of the inspection optical system instead of the inspection-target photomask blank, the (B1) to (B8) steps are carried out on one kind of pinhole defect or at least two kinds of pinhole defects with different widths. Then, by using obtained ΔS and Wsig, Ssat obtained in the (A7) step, and the above-described known width Wact instead of Wcal, T is calculated from the above expression (1). For the pinhole defect, the constant T calculated in the range of 0.5≤T≤0.6 according to the film structure or the depth of the pinhole defect (thickness of the thin film) can be used in this manner.

Specifically, in the present invention, in order to decide T in the above expression (1) in advance, the following (C1) to (C9) steps can be carried out.

(C1) a step of preparing the standard photomask blank having a pinhole defect whose width Wact is known and is smaller than the nominal resolution of the inspection optical system, (C2) a step of aligning the position of the pinhole defect with the inspection position of the inspection optical system, (C3) a step of setting the optical condition of the inspection optical system to the optical condition set in the (A3) step, (C4) a step of irradiating the standard photomask blank with the inspection light, (C5) a step of collecting reflected light of the region of the standard photomask blank irradiated with the inspection light through the objective lens of the inspection optical system as a magnified image of the region, (C6) a step of identifying an intensity change part in the light intensity distribution profile of the magnified image, (C7) a step of obtaining the difference ΔS between the maximum value and the minimum value of the light intensity of the intensity change part, (C8) a step of identifying both ends of the intensity change part as the edges of the defect and obtaining the width of the intensity change part as the apparent width Wsig of the pinhole defect, and (C9) a step of calculating the constant T from the apparent width Wsig of the defect and the differences Ssat and ΔS in the light intensity on the basis of the following expression (1-1).

$$Wact = Wsig \times (\Delta S/Ssat)^T \qquad (1\text{-}1)$$

The constant T may be obtained by actually using a photomask blank having a defect such as a programmed defect and carrying out the above-described steps or may be obtained through estimation by carrying out the above-described steps on the basis of optical simulation. Furthermore, with a stable inspection optical system, the constant T does not need to be obtained for each of the respective photomask blanks of inspection targets and it is also possible to apply the obtained constant T to evaluation of the defect size of plural inspection-target photomask blanks.

If plural defects of inspection targets exist, as shown in FIG. 4, it is determined whether inspection of all of the defects of inspection targets has ended as a step S108 according to need. If the inspection has not yet ended, as a step S109, a defect that has not yet been inspected is identified and the position of the defect to be inspected next is specified. Then, the processing returns to the step S105 and the steps S105 to S108 are repeated. When the inspection of all of the defects of inspection targets ends, the evaluation of the defect size of the photomask blank is ended.

In the (A4) step or the (B4) step, it is preferable to irradiate the photomask blank with the inspection light while the photomask blank is placed on a stage that allows the photomask blank to move in the in-plane direction thereof. Furthermore, it is preferable to irradiate the photomask blank with the inspection light by oblique illumination in which the optical axis of the inspection light is inclined to the inspected surface of the photomask blank.

Furthermore, in the (A5) step or the (B5) step, it is preferable for the inspection optical system to include a spatial filter that partly blocks light passing through substantially the pupil position of the objective lens, i.e. a so-called pupil filter, and it is preferable to collect the reflected light through the spatial filter.

In the first embodiment, an example of the case in which the edge part of a defect is observed as the boundary between a dark part and a bright part in an observation image of the defect is described. However, in the case of a pinhole defect existing in a thin film with a comparatively-large film thickness (e.g. thickness of 30 to 100 nm) like the optical thin film over the substrate of the photomask blank shown in FIG. 2B, i.e. a comparatively-deep pinhole defect (e.g. with depth of 20 to 100 nm), the edge part of the defect is often not observed as the boundary between a dark part and a bright part in an observation image. A method for evaluating the size of the pinhole defect in such a case (second embodiment) will be described next.

In the second embodiment, the step S103, particularly the (A7) step and the (A8) step, is different from the first embodiment. In the second embodiment, the following (A7a) step is included in the step S103 instead of the (A7) step.

(A7a) a step of obtaining difference Ssat between the maximum value of the light intensity of an intensity change part and the light intensity at the central part of the intensity change part in the width direction.

Furthermore, the step S103 of the second embodiment may include the following (A8a) step instead of the (A8) step.

(A8a) a step of guessing a threshold of a range corresponding to the width of the defect in the light intensity distribution profile of the intensity change part and obtaining the width of the light intensity distribution profile at the threshold, specifically the width between the positions corresponding to ½ of the above-described difference Ssat in the light intensity distribution profile of the intensity change part, i.e. a half width (full width at half maximum), as the apparent width Wsig of the defect.

Figure 6:
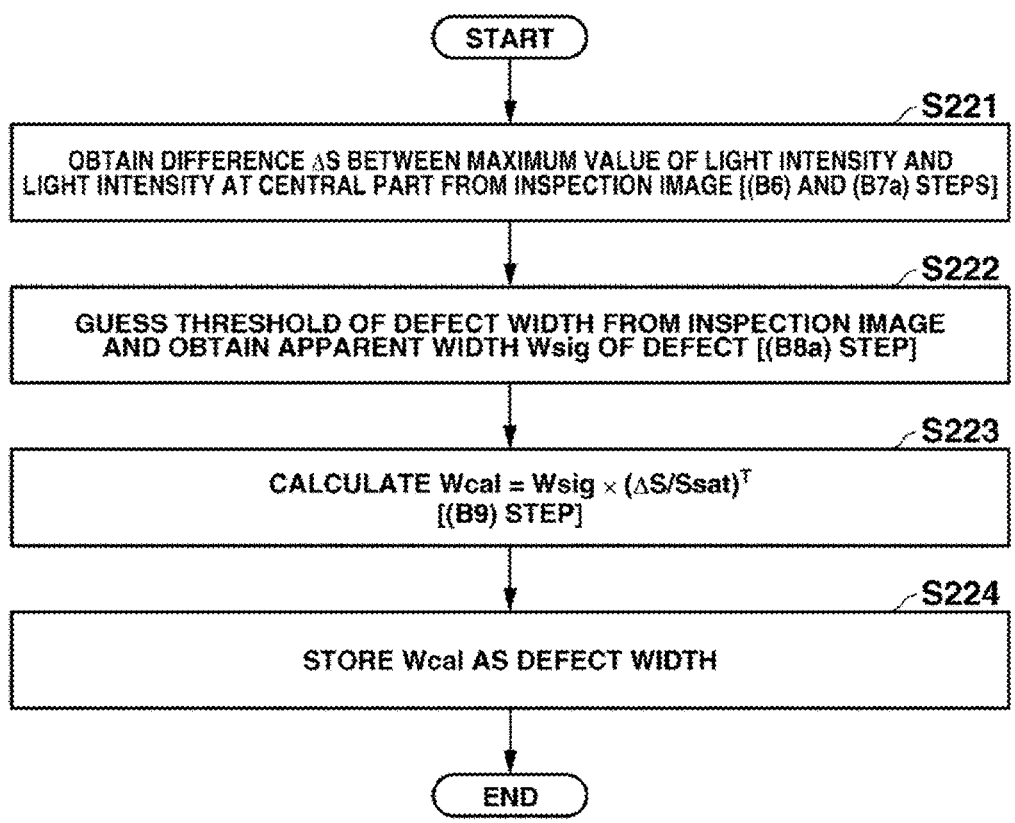
FIG. 6 is a flowchart showing another example (second embodiment) of the processing of obtaining the width Wcal of a defect in the evaluation method of the defect size of the photomask blank.

Furthermore, in the second embodiment, the step S107 is different from the first embodiment. The details of the flow of the processing of obtaining the width Wcal of the defect in the step S107 of the second embodiment will be described along a flowchart shown in FIG. 6. First, as a step S221, an intensity change part in the light intensity distribution profile of a magnified image is identified ((B6) step) and difference ΔS between the maximum value of the light intensity of the intensity change part and the light intensity at the central part of the intensity change part in the width direction is obtained ((B7a) step). Furthermore, as a step S222, a threshold of a range corresponding to the width of the pinhole defect in the light intensity distribution profile of the intensity change part is guessed and the width of the light intensity distribution profile at the threshold, specifically the width between the positions corresponding to ½ of the above-described difference ΔS in the light intensity distribution profile of the intensity change part, i.e. a half width (full width at half maximum), is obtained as the apparent width Wsig of the pinhole defect ((B8a) step).

Next, as a step S223, Wcal is calculated on the basis of the above expression (1) by using Ssat, ΔS, and Wsig obtained in the (A7a) step, the (B7a) step, and the (B8a) step, and Wcal is estimated as the width of the defect ((B9) step). Then, according to need, as a step S224, obtained Wcal is recorded as the width of the defect. Furthermore, in the second embodiment, the following (C7a) step and (C8a) step are applied instead of the (C7) step and the (C8) step in the first embodiment.

(C7a) a step of obtaining the difference ΔS between the maximum value of the light intensity of an intensity change part and the light intensity at the central part of the intensity change part in the width direction, and (C8a) a step of obtaining the width between the positions of ½ of the above-described difference ΔS of the light intensity distribution profile of the intensity change part as the apparent width Wsig of the pinhole defect.

Except for the above-described differences, as the other steps, the same steps as those in the first embodiment can be applied also in the second embodiment.

According to the present invention, the defect size can be effectively evaluated regarding a defect having a width smaller than the nominal resolution of the inspection optical system. The width of the defect as the evaluation target is normally at least 30 nm and preferably at least 40 nm. Furthermore, the width of the defect as the evaluation target is not particularly limited as long as it is smaller than the nominal resolution. However, whereas it is not easy for the related-art methods to evaluate a defect with a width of up to 200 nm, particularly up to 100 nm, and up to 60 nm above all, the present invention is effective even for evaluation of the size of such a minute defect. Moreover, also when the width of the defect as the evaluation target is at least the nominal resolution, the evaluation of the defect size by the present invention is possible. If the width is at least the nominal resolution, the upper limit of the width of the defect as the evaluation target is normally up to 1000 nm although not particularly limited.

By applying the evaluation method of the defect size according to the present invention to defect inspection of photomask blanks, photomask blanks that do not include a defect with a size surpassing a predetermined size criterion can be selected on the basis of information on the defect size obtained by the evaluation method. Furthermore, the information on the defect size obtained by the evaluation method of the defect size according to the present invention can be given to the photomask blank by a method of adding an inspection tag thereto. Moreover, it is also possible to select photomask blanks that do not include a defect with a size surpassing a predetermined size criterion on the basis of the information given to the photomask blanks. Furthermore, the evaluation method of the defect size according to the present invention can be carried out in a manufacturing method of a photomask blank in which at least one layer of a thin film is formed over a substrate and can be applied to evaluation of the size of a defect in the surface of the photomask blank in which at least one layer of the thin film is formed over the substrate. In the case of the related arts, it is difficult to evaluate the size of a defect smaller than the lower limit of the resolution by an optical defect detection method and therefore whether the photomask blank is accepted or rejected regarding product specs must be strictly determined in order to ship favorable photomask blanks. However, by evaluating the defect size of the photomask blank by the method of the present invention, the correct size can be determined about a defect smaller than the resolution limit and thus whether the photomask blank is accepted or rejected regarding product specs can be determined more accurately. Furthermore, this also enables improvement in the yield.

As above, the method for evaluating the size of a defect existing in the surface of a photomask blank is described. However, when the optical principle thereof is considered, it will be easily understood that, in the present invention, e.g. a semiconductor wafer over which various kinds of metal films are formed or a recording medium in which various kinds of metal films and optical thin films are formed over a substrate can be applied as an inspection-target object instead of a photomask blank and the evaluation method of the present invention can be favorably applied to an inspection-target object having a depression part such as a pinhole defect in its surface.

Examples will be shown below to specifically describe the present invention. However, the present invention is not limited to the following Examples.

EXAMPLE 1

As a specific example of the first embodiment, evaluation of the following defect size was carried out. An inspection optical system like that shown in FIG. 3 was used and the inspection wavelength was set to 248 nm. Furthermore, the illumination region control aperture AP1 was controlled to employ oblique illumination, and the aperture stop AP2 was set fully open to set an image-forming optical condition of NA=0.75. In this inspection optical system, the nominal resolution is obtained on the basis of the following expression and is about 202 nm.

resolution=$k_1 \times \lambda$/NA ($k_1$=0.61, $\lambda$=248, NA=0.75)

As the (A1) step, a photomask blank in which a programmed defect that had a width of at least the nominal resolution of the inspection optical system and had a 1000-nm or 2000-nm square shape was formed was prepared as a reference photomask blank. Then, the (A2) to (A7) steps and the (A8) step were carried out on the prepared reference photomask blank.

Figure 7A:
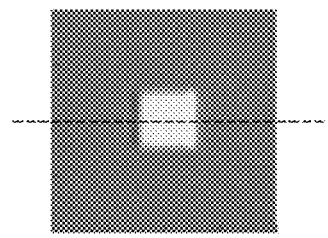
FIGS. 7A and 7C are observation images of defects in Example 1 and FIGS. 7B and 7D are graphs showing change in the light intensity in the observation images.
Figure 7B:
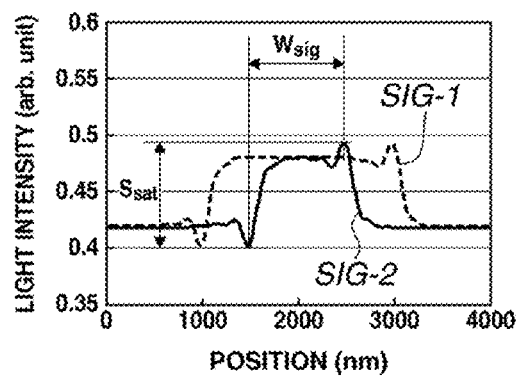
Figure 7C:
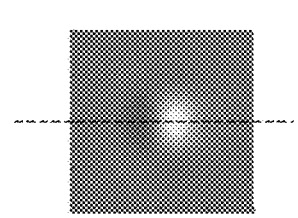
Figure 7D:
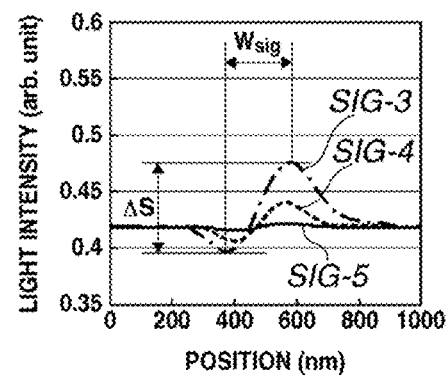

FIGS. 7A and 7C are observation images of pinhole defects with a depth of about 4 to 5 nm and FIGS. 7B and 7D are graphs showing change in the light intensity in the obtained observation images. FIG. 7A is an observation image (magnified image) of the programmed defect with a width of 1000 nm. FIG. 7B is a diagram showing change in the light intensity along one direction (line A-A') passing through substantially the center of an intensity change part in the light intensity distribution profile of the magnified image of FIG. 7A. The change in the light intensity along the line A-A' in FIG. 7A is shown by a curve SIG-2 in FIG. 7B. In this case, as shown in FIG. 7A, the edge part of the defect is clearly observed as the boundary between a dark part and a bright part in the observation image. Thus, on the basis of this fact, the difference Ssat between the maximum value and the minimum value of the light intensity and the apparent width Wsig of the defect are obtained from the observation image. Furthermore, in FIG. 7B, a curve SIG-1 shows change in the light intensity obtained from the programmed defect having a 2000-nm square shape similarly to the programmed defect having a 1000-nm square shape, and it proves that the difference Ssat between the maximum value and the minimum value of the light intensity obtained from the programmed defect having the 2000-nm square shape is substantially equivalent to Ssat obtained with the programmed defect having the 1000-nm square shape.

FIG. 7C is an observation image (magnified image) of a defect having a 200-nm square shape. FIG. 7D is a diagram showing change in the light intensity along one direction (line B-B') passing through substantially the center of an intensity change part in the light intensity distribution profile of the magnified image of FIG. 7C. The change in the light intensity along the line B-B' in FIG. 7C is shown by a curve SIG-3 in FIG. 7D. Furthermore, in FIG. 7D, curves SIG-4 and SIG-5 show change in the light intensity obtained from defects having a 100-nm square shape and a 40-nm square shape, respectively, similarly to the defect having the 200-nm square shape. In the defect with a size smaller than the nominal resolution of the inspection optical system, the edge part of the defect is observed as the boundary between a dark part and a bright part in the observation image as shown in FIG. 7C although being not so clear as that of a defect having a sufficiently large size like that shown in FIG. 7A. Thus, the difference $\Delta S$ between the maximum value and the minimum value of the light intensity and the apparent width Wsig of the defect can be obtained.

Figure 8A:
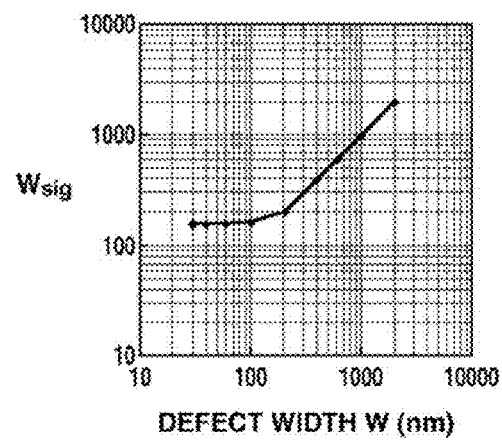
FIGS. 8A to 8C are graphs showing the relationships between the actual defect width and the respective measured values or a calculated value in Example 1.
Figure 8B:
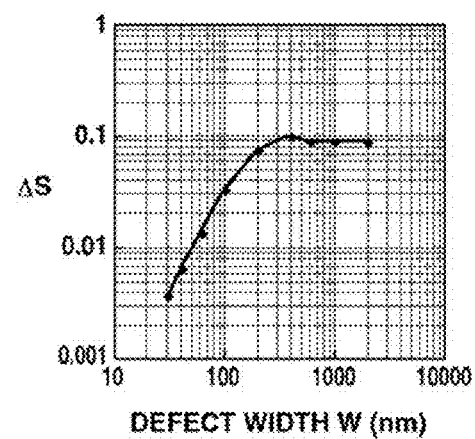
Figure 8C:
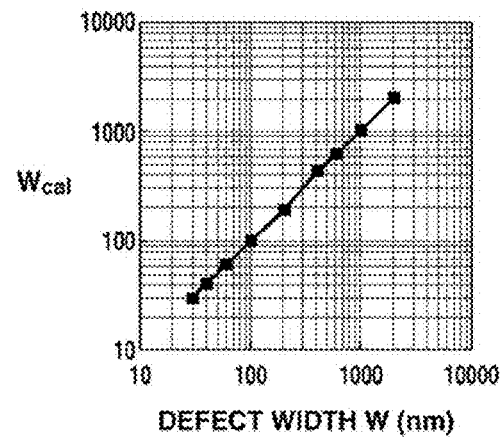

FIGS. 8A to 8C are graphs showing the relationships between the actual defect width and the respective measured values or the calculated value. For the calculation of the defect width, a value of T=0.53 obtained by carrying out the (C1) to (C9) steps on the basis of optical simulation in advance was used as the constant T in the above-described expression (1). FIG. 8A is a graph obtained by plotting the apparent width Wsig of the defect with respect to the actual defect width W. FIG. 8B is a graph obtained by plotting the difference $\Delta S$ between the maximum value and the minimum value of the light intensity of the defect with respect to the actual defect width W. FIG. 8C is a graph obtained by plotting Wcal calculated on the basis of the above-described expression (1) with respect to the actual defect width W. Wsig is the same as the actual defect width W in the size region at least the nominal resolution of the inspection optical system. However, in the size region smaller than the nominal resolution of the inspection optical system, Wsig is an almost constant value and does not correspond with the actual defect width W. On the other hand, the difference $\Delta S$ between the maximum value and the minimum value of the light intensity of the defect converges on a constant value Ssat and does not show size dependence in the size region of at least the nominal resolution of the inspection optical system, and decreases along with decrease in the actual defect width W in the size region smaller than the nominal resolution of the inspection optical system. Wcal calculated on the basis of the above-described expression (1) of the present invention defined from these relationships substantially corresponds with the actual defect width with an error of up to 10% in the size region smaller than the nominal resolution of the inspection optical system and in the size region of at least the nominal resolution of the inspection optical system. Thus, it proves that the actual defect width W can be accurately evaluated by the evaluation method of the present invention in an error range in which no problem is caused practically.

EXAMPLE 2

As a specific example of the second embodiment, evaluation of the following defect size was carried out. An inspection optical system like that shown in FIG. 3 was used and the inspection wavelength was set to 248 nm. Furthermore, the illumination region control aperture AP1 was controlled to employ oblique illumination, and the aperture stop AP2 was set fully open to set an image-forming optical condition of NA=0.75. The nominal resolution of this inspection optical system is about 202 nm as with Example 1. As the (A1) step, a photomask blank in which a programmed defect that had a width of at least the nominal resolution of the inspection optical system and had a 600-nm square shape was formed was prepared as a reference photomask blank. Then, the (A2) to (A6) steps, the (A7a) step, and the (A8a) step were carried out on the prepared reference photomask blank.

Figure 9:
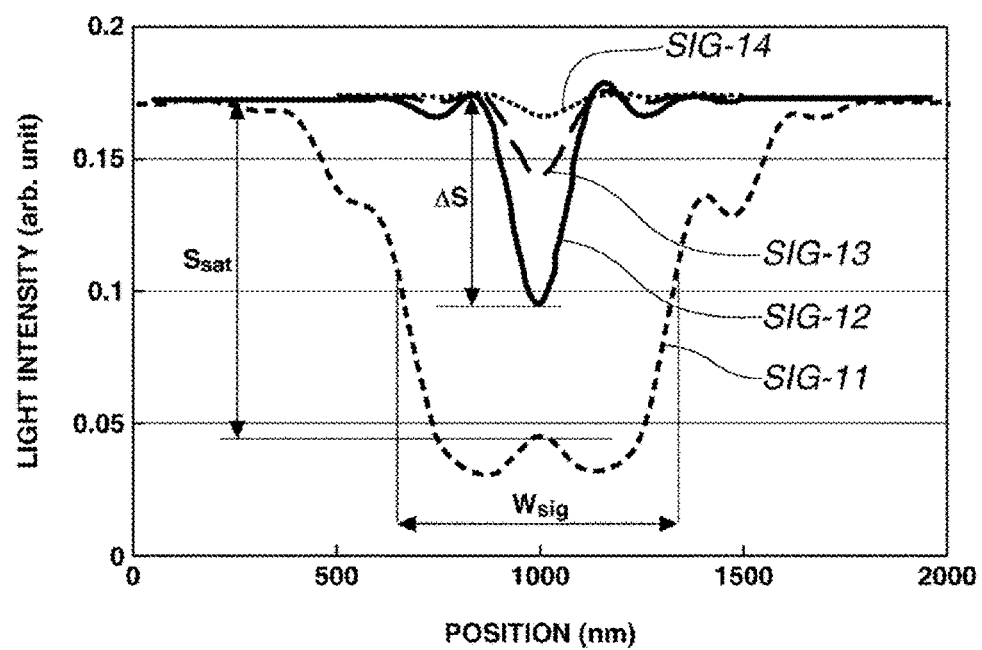
FIG. 9 is a graph showing change in the light intensity in observation images of defects in Example 2.

FIG. 9 is diagram showing change in the light intensity along one direction passing through substantially the center of an intensity change part in the light intensity distribution profile of an observation image (magnified image) of the programmed defect (pinhole defect) with a depth of 75 nm and a width of 600 nm. This change is shown by a curve SIG-11. On the other hand, curves SIG-12, SIG-13, and SIG-14 show change in the light intensity obtained from defects having a 100-nm square shape, a 60-nm square shape, and a 30-nm square shape, respectively, similarly to the programmed defect having the 600-nm square shape.

As shown in FIG. 9, as a light intensity difference of the intensity change part, the difference Ssat or ΔS between the maximum value of the light intensity of the intensity change part and the light intensity at the central part of the intensity change part in the width direction can be obtained. In this case, if the light intensity at the central part of the intensity change part in the width direction shows such a change as to become higher than that at the part around the central part as shown by the curve SIG-11, the difference between the maximum value of the light intensity of the intensity change part and the light intensity at the top of a sub-peak at the central part in the width direction is obtained as the difference Ssat or the difference ΔS. If change in the light intensity at the central part in the width direction like that shown in the curve SIG-11 does not exist as shown by the curves SIG-12 to SIG-14, the difference between the maximum value and the minimum value of the light intensity of the intensity change part is obtained as the difference Ssat or the difference ΔS. Furthermore, as shown in FIG. 9, the width between the positions corresponding to ½ of the difference Ssat or the difference ΔS of the light intensity distribution profile of the intensity change part, i.e. a half width (full width at half maximum), can be obtained as the apparent width Wsig of the defect.

Figure 10A:
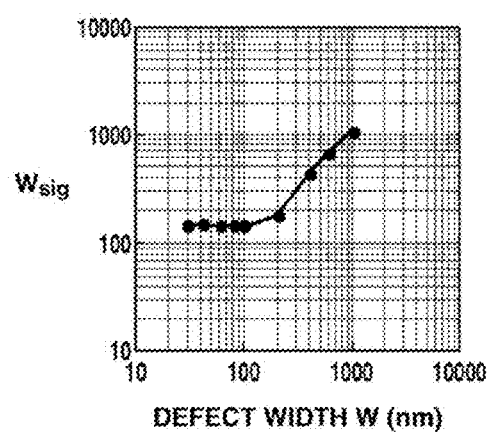
FIGS. 10A to 10C are graphs showing the relationships between the actual defect width and the respective measured values or a calculated value in Example 2.
Figure 10B:
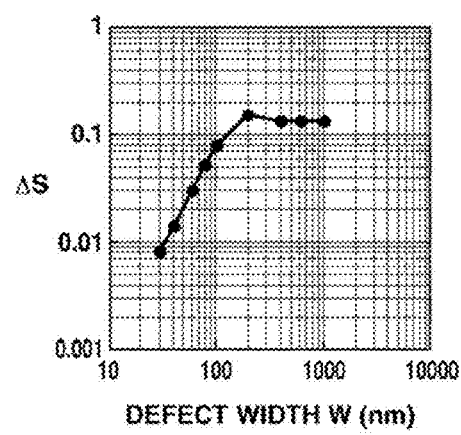
Figure 10C:
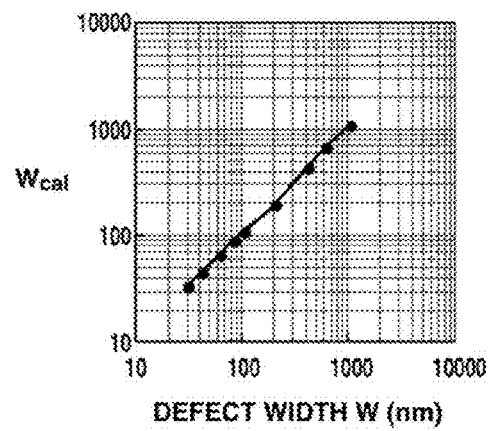

FIGS. 10A to 10C are graphs showing the relationships between the actual defect width and the respective measured values or the calculated value. For the calculation of the defect width, a value of T=0.56 obtained by carrying out the (C1) to (C6) steps, the (C7a) step, the (C8a) step, and the (C9) step on the basis of optical simulation in advance was used as the constant T in the above-described expression (1). FIG. 10A is a graph obtained by plotting the apparent width Wsig of the defect with respect to the actual defect width W. FIG. 10B is a graph obtained by plotting the difference ΔS between the maximum value and the minimum value of the light intensity of the defect with respect to the actual defect width W. FIG. 10C is a graph obtained by plotting Wcal calculated on the basis of the above-described expression (1) with respect to the actual defect width W. Wsig is the same as the actual defect width W in the size region of at least the nominal resolution of the inspection optical system. However, in the size region smaller than the nominal resolution of the inspection optical system, Wsig is an almost constant value and does not correspond with the actual defect width W. On the other hand, the difference ΔS between the maximum value and the minimum value of the light intensity of the defect converges on a constant value Ssat and does not show size dependence in the size region of at least the nominal resolution of the inspection optical system, and decreases along with decrease in the actual defect width W in the size region smaller than the nominal resolution of the inspection optical system. Wcal calculated on the basis of the above-described expression (1) of the present invention defined from these relationships substantially corresponds with the actual defect width with an error of up to 10% in the size region smaller than the nominal resolution of the inspection optical system and in the size region of at least the nominal resolution of the inspection optical system. Thus, it proves that the actual defect width W can be accurately evaluated by the evaluation method of the present invention in an error range in which no problem is caused practically.

Although some preferred embodiments have been described, many modifications and variations may be made thereto in light of the above teachings. It is therefore to be understood that the invention may be practiced otherwise than as specifically described without departing from the scope of the appended claims.

Japanese Patent Application No. 2014-217386 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An evaluation method of defect size of a photomask blank, the evaluation method being a method for evaluating size of a defect in a surface of the photomask blank in which at least one layer of a thin film is formed over a substrate, the evaluation method comprising the steps of:
   (A1) preparing a reference photomask blank having a defect whose width is known and is at least nominal resolution of an inspection optical system;
   (A2) aligning a position of the defect with an inspection position of the inspection optical system;
   (A3) setting an optical condition of the inspection optical system;
   (A4) irradiating the reference photomask blank with inspection light;
   (A5) collecting reflected light of a region of the reference photomask blank irradiated with the inspection light through an objective lens of the inspection optical system as a magnified image of the region;
   (A6) identifying an intensity change part in a light intensity distribution profile of the magnified image;

(A7) obtaining difference Ssat between a maximum value and a minimum value of light intensity of the intensity change part;

(B1) preparing an inspection-target photomask blank having a pinhole defect whose width is smaller than the nominal resolution of the inspection optical system;

(B2) aligning a position of the pinhole defect with the inspection position of the inspection optical system;

(B3) setting the optical condition of the inspection optical system to the optical condition set in the (A3) step;

(B4) irradiating the inspection-target photomask blank with inspection light;

(B5) collecting reflected light of a region of the inspection-target photomask blank irradiated with the inspection light through the objective lens of the inspection optical system as a magnified image of the region;

(B6) identifying an intensity change part in a light intensity distribution profile of the magnified image;

(B7) obtaining difference ΔS between a maximum value and a minimum value of light intensity of the intensity change part;

(B8) identifying both ends of the intensity change part as edges of the pinhole defect and obtaining width of the intensity change part as apparent width Wsig of the pinhole defect; and (B9) calculating Wcal from the apparent width Wsig of the pinhole defect and the differences Ssat and ΔS in the light intensity on the basis of the following expression (1) and estimating Wcal as width of the pinhole defect, $$W\mathrm{cal}=W\mathrm{sig}\times(\Delta S/S\mathrm{sat})^T \qquad (1)$$

wherein T is a constant satisfying a relationship of $0.5 \leq T \leq 0.6$.

2. The evaluation method of claim 1, wherein a photomask blank in which a programmed defect having a predetermined width is formed is used as the reference photomask blank.

3. The evaluation method of claim 1, wherein the (A1) to (A7) steps or the (A1) to (A7a) steps are carried out on the basis of optical simulation to obtain the difference Ssat in the light intensity.

4. The evaluation method of claim 1, wherein the inspection light is light with a wavelength of 210 to 550 nm.

5. The evaluation method of claim 1, wherein, in the (A4) step or the (B4) step, the photomask blank is irradiated with the inspection light while being placed on a stage that allows the photomask blank to move in in-plane direction of the photomask blank.

6. The evaluation method of claim 1, wherein, in the (A4) step or the (B4) step, the photomask blank is irradiated with the inspection light by oblique illumination in which an optical axis of the inspection light is inclined to an inspected surface of the photomask blank.

7. The evaluation method of claim 1, wherein, in the (A5) step or the (B5) step, the inspection optical system includes a spatial filter that partly blocks light passing through substantially a pupil position of the objective lens and collects the reflected light through the spatial filter.

8. A selection method of a photomask blank, comprising the step of:
selecting a photomask blank that does not include a defect with size surpassing a predetermined size criterion on the basis of information on defect size obtained by the evaluation method of claim 1.

9. A manufacturing method of a photomask blank, comprising the steps of:
forming at least one layer of a thin film over a substrate; and
evaluating size of a defect in a surface of a photomask blank in which the at least one layer of the thin film is formed over the substrate by the evaluation method of claim 1.

10. An evaluation method of defect size of a photomask blank, the evaluation method being a method for evaluating size of a defect in a surface of the photomask blank in which at least one layer of a thin film is formed over a substrate, the evaluation method comprising the steps of:

(A1) preparing a reference photomask blank having a defect whose width is known and is at least nominal resolution of an inspection optical system;

(A2) aligning a position of the defect with an inspection position of the inspection optical system;

(A3) setting an optical condition of the inspection optical system;

(A4) irradiating the reference photomask blank with inspection light;

(A5) collecting reflected light of a region of the reference photomask blank irradiated with the inspection light through an objective lens of the inspection optical system as a magnified image of the region;

(A6) identifying an intensity change part in a light intensity distribution profile of the magnified image;

(A7a) obtaining difference Ssat between a maximum value of light intensity of the intensity change part and the light intensity at a central part of the intensity change part in width direction;

(B1) preparing an inspection-target photomask blank having a pinhole defect whose width is smaller than the nominal resolution of the inspection optical system;

(B2) aligning a position of the pinhole defect with the inspection position of the inspection optical system;

(B3) setting the optical condition of the inspection optical system to the optical condition set in the (A3) step;

(B4) irradiating the inspection-target photomask blank with inspection light;

(B5) collecting reflected light of a region of the inspection-target photomask blank irradiated with the inspection light through the objective lens of the inspection optical system as a magnified image of the region;

(B6) identifying an intensity change part in a light intensity distribution profile of the magnified image;

(B7a) obtaining difference ΔS between a maximum value of light intensity of the intensity change part and the light intensity at a central part of the intensity change part in width direction;

(B8a) obtaining width between positions of ½ of the difference ΔS of the light intensity distribution profile of the intensity change part as apparent width Wsig of the pinhole defect; and (B9) calculating Wcal from the apparent width Wsig of the pinhole defect and the differences Ssat and ΔS in the light intensity on the basis of the following expression (1) and estimating Wcal as width of the pinhole defect, $$W\mathrm{cal}=W\mathrm{sig}\times(\Delta S/S\mathrm{sat})^T \qquad (1)$$

wherein T is a constant satisfying a relationship of $0.5 \leq T \leq 0.6$.

11. The evaluation method of claim 10, wherein a photomask blank in which a programmed defect having a predetermined width is formed is used as the reference photomask blank.

12. The evaluation method of claim 10, wherein the (A1) to (A7) steps or the (A1) to (A7a) steps are carried out on the basis of optical simulation to obtain the difference Ssat in the light intensity.

13. The evaluation method of claim 10, wherein the inspection light is light with a wavelength of 210 to 550 nm.

14. The evaluation method of claim 10, wherein, in the (A4) step or the (B4) step, the photomask blank is irradiated with the inspection light while being placed on a stage that allows the photomask blank to move in in-plane direction of the photomask blank.

15. The evaluation method of claim 10, wherein, in the (A4) step or the (B4) step, the photomask blank is irradiated with the inspection light by oblique illumination in which an optical axis of the inspection light is inclined to an inspected surface of the photomask blank.

16. The evaluation method of claim 10, wherein, in the (A5) step or the (B5) step, the inspection optical system includes a spatial filter that partly blocks light passing through substantially a pupil position of the objective lens and collects the reflected light through the spatial filter.

17. A selection method of a photomask blank, comprising the step of:
  selecting a photomask blank that does not include a defect with size surpassing a predetermined size criterion on the basis of information on defect size obtained by the evaluation method of claim 10.

18. A manufacturing method of a photomask blank, comprising the steps of:
  forming at least one layer of a thin film over a substrate; and
  evaluating size of a defect in a surface of a photomask blank in which the at least one layer of the thin film is formed over the substrate by the evaluation method of claim 10.

* * * * *